United States Patent
Halinen et al.

(10) Patent No.: US 11,931,177 B2
(45) Date of Patent: *Mar. 19, 2024

(54) CAPACITIVE LEADWIRE FOR PHYSIOLOGICAL PATIENT MONITORING

(71) Applicant: General Electric Company, Schenectady, NY (US)

(72) Inventors: Jussi Halinen, Helsinki (FI); Ville Vartiovaara, Helsinki (FI); Otto Valterri Pekander, Helsinki (FI); Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/971,193

(22) Filed: Oct. 21, 2022

(65) Prior Publication Data

US 2023/0043358 A1 Feb. 9, 2023

Related U.S. Application Data

(63) Continuation of application No. 15/387,226, filed on Dec. 21, 2016, now Pat. No. 11,547,355.

(51) Int. Cl.
| | |
|---|---|
| *A61B 5/00* | (2006.01) |
| *A61B 5/08* | (2006.01) |
| *A61B 5/25* | (2021.01) |
| *A61B 5/30* | (2021.01) |

(Continued)

(52) U.S. Cl.
CPC .......... *A61B 5/6823* (2013.01); *A61B 5/0809* (2013.01); *A61B 5/0816* (2013.01); *A61B 5/25* (2021.01); *A61B 5/30* (2021.01); *A61B 5/303* (2021.01); *H05K 1/0326* (2013.01); *H05K 1/0346* (2013.01); *H05K 1/162* (2013.01); *H05K 1/167* (2013.01); *A61B 2562/222* (2013.01); *H05K 2201/0129* (2013.01); *H05K 2201/09227* (2013.01)

(58) Field of Classification Search
CPC ........ A61B 5/6823; A61B 5/303; A61B 5/30; A61B 5/25; A61B 5/0809; A61B 5/0816; A61B 2562/222; H05K 1/0326; H05K 1/0346; H05K 1/162; H05K 1/167; H05K 2201/0129; H05K 2201/09227
See application file for complete search history.

(56) References Cited

U.S. PATENT DOCUMENTS

| | | | |
|---|---|---|---|
| 6,377,845 B1 * | 4/2002 | Kinast | A61B 5/30 600/547 |
| 7,092,750 B2 * | 8/2006 | Van Ess | A61B 5/303 600/509 |

(Continued)

*Primary Examiner* — Eun Hwa Kim
*Assistant Examiner* — Catherine C. Premraj

(57) ABSTRACT

A leadwire for physiological patient monitoring is provided that transfers potentials received at a chest electrode to a data acquisition device. The leadwire includes an electrode end connectable to the chest electrode and a first conductive layer extending from the electrode end. The leadwire also has a device end connectable to a data acquisition device and a second conductive layer extending from the device end. The first conductive layer is galvanically isolated from the second conductive layer such that the first conductive layer and the second conductive layer form a capacitor.

18 Claims, 5 Drawing Sheets

(51) Int. Cl.
*H05K 1/03* (2006.01)
*H05K 1/16* (2006.01)

(56) References Cited

U.S. PATENT DOCUMENTS

| | | | |
|---|---|---|---|
| 2010/0114271 A1* | 5/2010 | Sommer | A61N 1/05 |
| | | | 174/110 R |
| 2012/0253340 A1* | 10/2012 | Stevenson | H03H 7/0123 |
| | | | 607/116 |
| 2013/0289376 A1* | 10/2013 | Lang | A61B 5/25 |
| | | | 427/2.12 |
| 2017/0006709 A1* | 1/2017 | Chen | G06F 30/392 |

* cited by examiner

CAPACITIVE LEADWIRE FOR PHYSIOLOGICAL PATIENT MONITORING

PRIORITY

This Application is a continuation of U.S. patent application Ser. No. 15/387,226, filed on Dec. 21, 2016, which is incorporated herein by reference in its entirety

BACKGROUND

This disclosure generally relates to medical monitoring systems and devices, and more specifically to leadwires for ECG and/or respiratory monitoring.

Electrocardiograms (ECGs) are graphic depictions of electrical activity in the heart, i.e. cardiac potentials. ECGs are produced by electrocardiographs which are available as stand alone devices, portable devices, and/or as integrated functions in various types of multi-vital sign monitoring devices. ECGs are depicted by time (ms) versus voltage (mV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient.

Respiration monitors are also available that use chest electrodes that are similar or identical to ECG electrodes. For example, respiration rate measurement may be determined using impedance pneumography, where a high-frequency A/C current is passed between at least two electrodes (often the right arm electrode and left arm electrode), including a driving electrode and a receiving electrode, on the patient's chest and an impedance between the electrodes is determined. Respiration is then monitored according to the changing impedance values as the patient breathes. As the patient inhales, air (which is an insulator) enters the lungs and causes the net impedance in the circuit to increase. When the patient exhales, air leaves the lungs and causes the impedance in the circuit to decrease.

Both electrocardiographs and respiration monitors (which may be separate devices or contained in a single device using a common set of electrodes) must have protection circuitry to protect the electronics of those devices from high voltage exposure due to operation of a defibrillator on a patient to which the monitoring devices are connected. Patients experiencing sudden cardiac arrest are treated with a defibrillation shock to the chest. The defibrillation shock is typically in the range of 3 to 5 kilovolts and 50 amps, but could be any value ranging from 300 volts to 5 kilovolts, and typically lasts between 5 and 20 milliseconds. A high voltage and current are necessary in order to stop the patient's heart from unproductive fluttering (fibrillating) and to allow the heart to restart effective pumping of blood. Typically, respiration monitors and electrocardiographs are separate from the defibrillator device, and the chest electrodes and leadwires are connected to the patient when the defibrillator delivers the shock. Thus, the electrocardiograph and respiration monitors must withstand the significant voltage and current of the defibrillation and continue working properly.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a leadwire for physiological patient monitoring is provided that transfers potentials received at a chest electrode to a data acquisition device. The leadwire includes an electrode end connectable to the chest electrode and a first conductive layer extending from the electrode end. The leadwire also has a device end connectable to a data acquisition device and a second conductive layer extending from the device end. The first conductive layer is galvanically isolated from the second conductive layer such that the first conductive layer and the second conductive layer form a capacitor.

One embodiment of a printed leadwire comprises a first conductive layer printed on a substrate, the first conductive layer extending from an electrode end connecting to a chest electrode, and a second conductive layer printed on the substrate and extending from a device end connecting to a data acquisition device. The first conductive layer is galvanically isolated from the second conductive layer such that the first conductive layer and the second conductive layer form a capacitor.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

As described above, electrocardiographs and respiration monitors must be configured to withstand the high voltage defibrillation pulses, which are on the order of 3 to 5 kilovolts and 50 amps and last for 5 to 20 milliseconds (which is a long time for electronic components to survive such high voltage). Thus, such monitoring devices are typically provided with defibrillation protection circuitry at their inputs which is designed to absorb the energy of the high voltage pulse before it reaches the sensitive electronics. Defibrillation protection in electrocardiograph and respiration monitoring devices has traditionally been implemented with resistors, which are large and expensive because they must be designed to cope with huge defibrillation power surges. Additionally, resistive components introduce thermal noise. For example, the energy travelling through an average 10 kiloohm resistor from a 5 kilovolt defibrillation pulse can cause the resistor to reach very high temperatures, such as internal temperatures reaching 200° Celsius or higher. This significant heating of the resistor causes it to break down.

The present inventors have recognized that the use of capacitive, or more generally reactive, impedance in place of or in addition to such passive resistive components enables the use of high impedance levels without inherent noise issues. Additionally, the present inventors have recognized that the leadwires themselves, which connect chest electrodes on the patient to data acquisition devices of patient monitors, can be created so that the length of the leadwire provides capacitive transmission of physiological signals recorded at the electrode. This allows for inclusion of a relatively large capacitive element providing significant protection against the defibrillation pulse without increasing the overall size of the leadwire or the data acquisition device.

In one embodiment developed by the inventors, the leadwires are printed elements having a first conductive layer and a second conductive layer printed on a flexible substrate, where the first conductive layer is galvanically isolated from second conductive layer such that the first conductive layer and the second conductive layer form a capacitor. Thus, the capacitive element can be relatively long, such as comprising a majority of the length of the leadwire, providing a relatively large capacitor without adding significant bulk as compared to a standard leadwire providing galvanic conduction.

Figure 1:
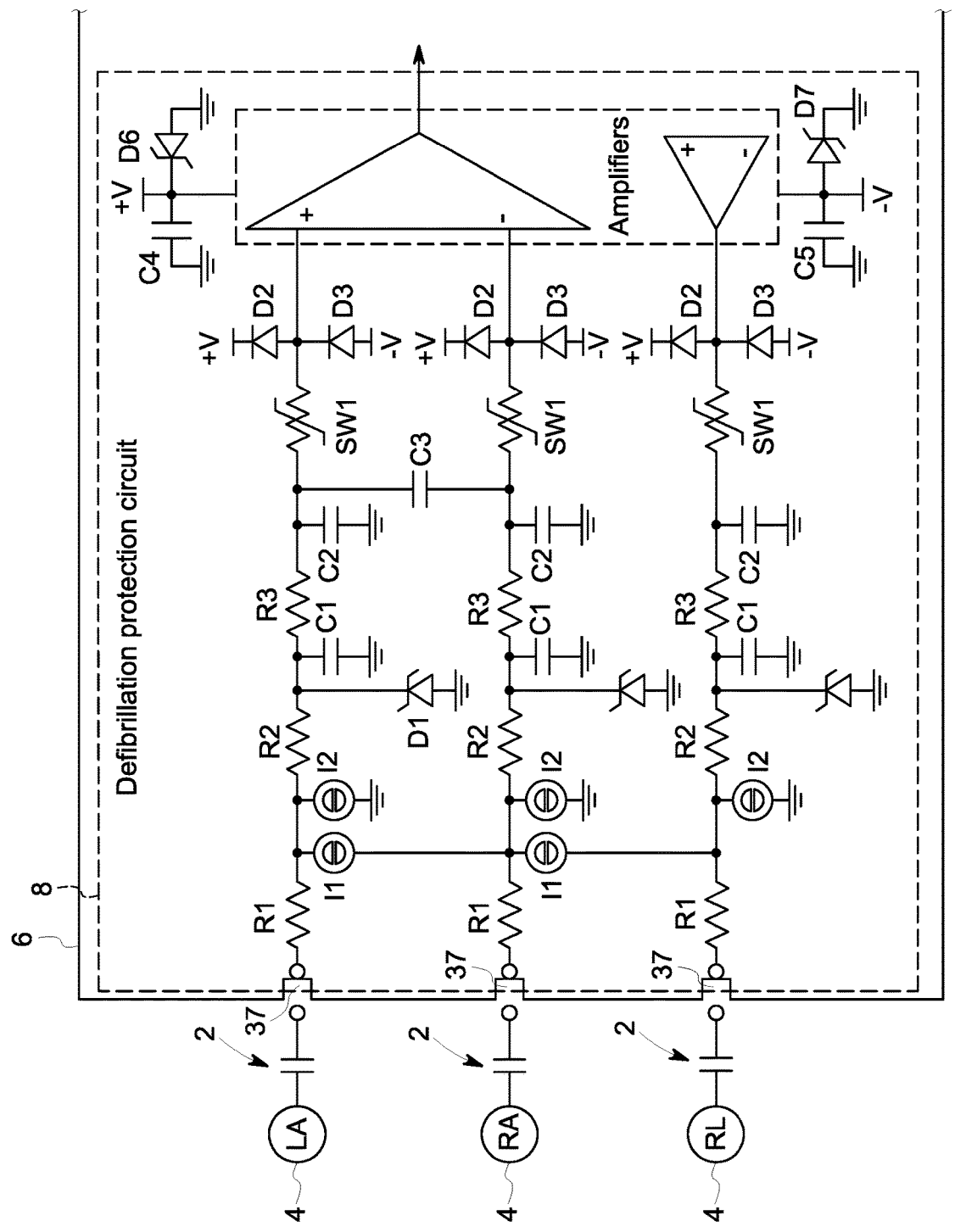
FIG. 1 depicts one embodiment of defibrillation protection circuitry in a data acquisition device and leadwires for physiological patient monitoring connectable to the defibrillation protection circuitry.

FIG. 1 includes a circuit diagram of an exemplary defibrillation protection circuit 8 provided at the input of a data acquisition device 6 for acquiring cardiac or respiration signals from a patient, and capacitive leadwires 2 that are connectable to the defibrillation protection circuit. The capacitive leadwires 2 connect chest electrodes 4 to the data acquisition device, where the defibrillation protection circuit 8 resides as a front end protection circuit. In the example, three chest electrodes 4 are depicted for purposes of explanation, which include the left arm electrode LA, right arm electrode RA, and right leg electrode RL. As will be understood by a person having ordinary skill in the art in light of this disclosure, any number of electrodes may be included and received by the data acquisition device 6. For example, in 12-lead ECG applications ten or more electrodes may be used and connected to the data acquisition device 6. In such embodiments, the defibrillation protection circuit 8 includes protection circuit elements for each input. The leadwires 2 may be disposable elements or reusable elements, and in a preferred embodiment removably connect to the data acquisition device 6, such as at a receptacle 37 in a housing of the data acquisition device 6.

In the depicted example, the defibrillation protection circuit 8 provided at the front end of the data acquisition device 6 includes a resistor $R_1$ at the galvanic connection point of each receptacle 37. For example, the resister $R_1$ may be in the range of 10 to 20 kiloohms, or even as high as 100 kiloohms. For each input, the resistor $R_1$ may be connected in series with one or more voltage absorption elements $I_1$ and $I_2$, which are configured to absorb at least a portion of the energy exiting the resistor $R_1$ during a defibrillation event. For example, $I_1$ and $I_2$ may be neon glow lamps, where a small radioactive dot inside a gas tube provides photons to stabilize the ionization voltage. Such neon glow lamps are commonly used in defibrillation protection circuits 8. Alternatively, $I_1$ and $I_2$ may be gas-discharge arrestor tubes or transient voltage suppressors, which are also known to be used for such purposes.

Resistors $R_2$ and $R_3$, along with capacitors $C_1$, $C_2$, and $C_3$ form low pass filters for each input. The diode $D_1$ limits the voltage to a lower level. For example, diode $D_1$ may be a Zener diode or an Avalanche diode, a metal oxide varistor, or a thyristor surge protector. The diode $D_1$ in conjunction with the capacitor $C_1$ provide the first part of a low pass filter. Capacitor $C_2$ acts as a common-mode filter, and capacitor $C_3$ provides differential filtering. Typically, capacitor $C_3$ is about ten times larger than capacitor $C_2$. A high-voltage signal-line protector $SW_1$ follows the low pass filter and is a switch that senses high voltage and turns on a clamp to reduce the amount of voltage permitted to reach the respective amplifier. In alternative embodiments, the current limiting element may instead be a current-limiting diode. Diodes $D_2$ and $D_3$ are electrostatic discharge protection diodes that clamp the amplifier input to the power supplies. Capacitor $C_4$ and Zener diode $D_6$ are connected to the amplifiers to absorb and clamp the positive voltage rail. Capacitor $C_5$ and Zener diode $D_7$ are also connected to the amplifiers in order to absorb and clamp the negative voltage rail.

The defibrillation protection circuit 8 depicted in FIG. 1 is just one example of a standard protection circuit often provided at the input of a patient monitor in order to absorb voltage during a defibrillation pulse so that the electronics of the patient monitor are not destroyed. A person having ordinary skill in the art will understand that any number of different electrical components and circuit arrangements may be provided to serve such purpose.

The defibrillation protection circuit 8 may be followed by an analog front end 9 (AFE) which filters and digitizes the analog signals that emerge from the defibrillation protection circuit 8, or may be incorporated into an AFE. Various analog front end designs are well known. In certain embodiments, the defibrillation protection circuit 8 and the analog front end 9 may be integrated into a single device or arrangement.

The inventors of the present application have recognized that such defibrillator protection circuits may be insufficient for providing protection from defibrillation pulses, especially as data acquisition devices 6 become smaller and it is desirable to reduce the size of the components and the overall circuit. Accordingly, the inventors have endeavored to provide a more robust defibrillation protection system that allows flexibility to decrease the size of the defibrillation protection circuit 8 provided in the data acquisition device 6 of the patient monitoring system. For example, in the context of wireless patient monitoring, it is desirable to provide a data acquisition device 6 that can be worn by or attached to the body of a patient. In such an embodiment, it is desirable to provide a small and light data acquisition device 6 that can wirelessly transmit physiological data gathered from the patient, such as ECG data or respiration data, to a hub device or host computer network associated with the patient physiological monitoring system.

In view of their recognition of the aforementioned problems and challenges in the relevant field, the inventors developed the capacitive leadwires 2 disclosed herein which provide defibrillation protection prior to the input of the data acquisition device 6, thus limiting the power surge that the defibrillation protection circuit 8 must handle. Accordingly, the footprint of the defibrillation protection circuit can be decreased, thereby decreasing the overall size of the data acquisition device 6.

Figure 2:
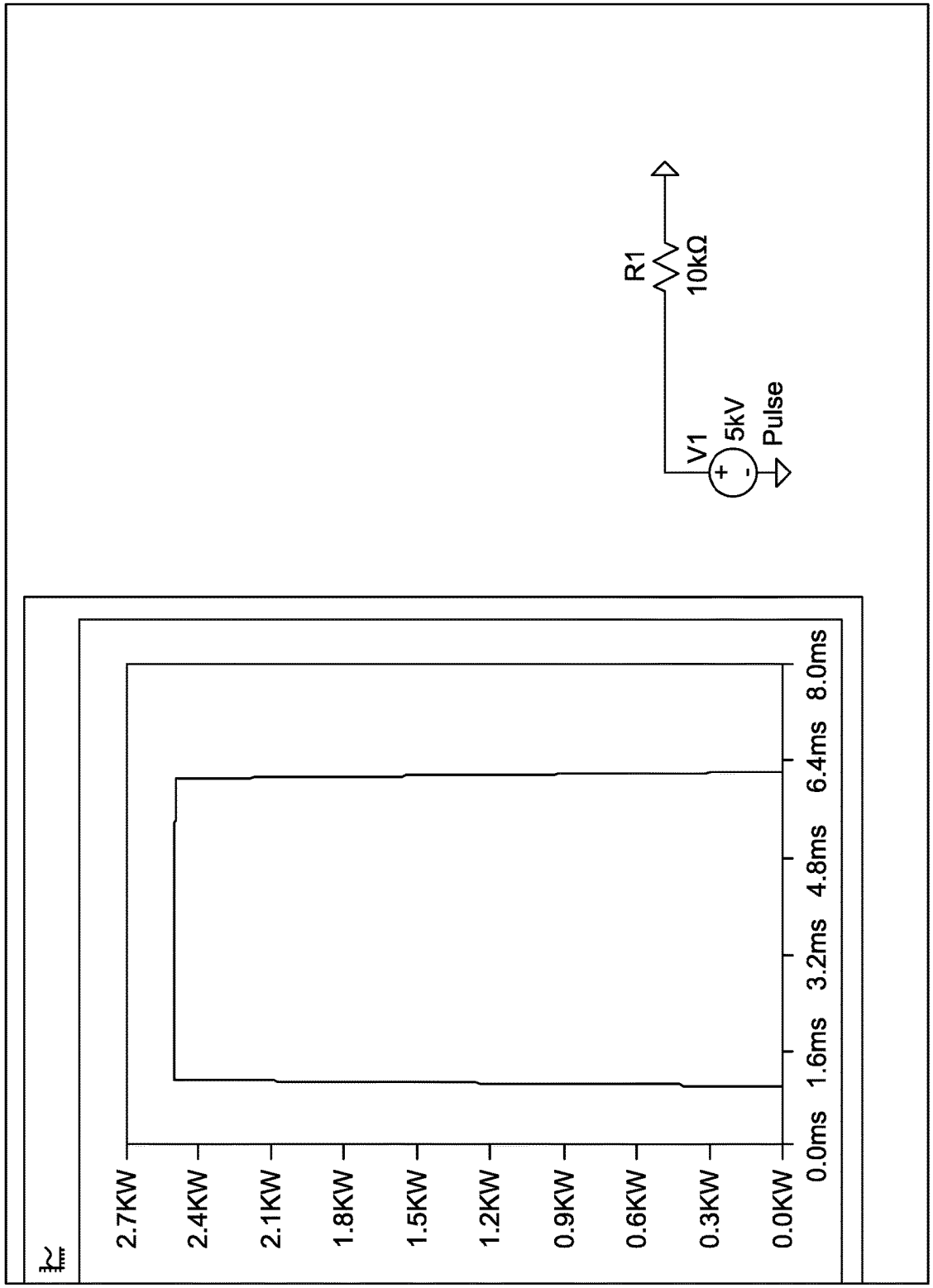
FIG. 2 is a graph depicting power measured at the output of a first resistor typically provided at the front end of a defibrillation protection circuit.
Figure 3:
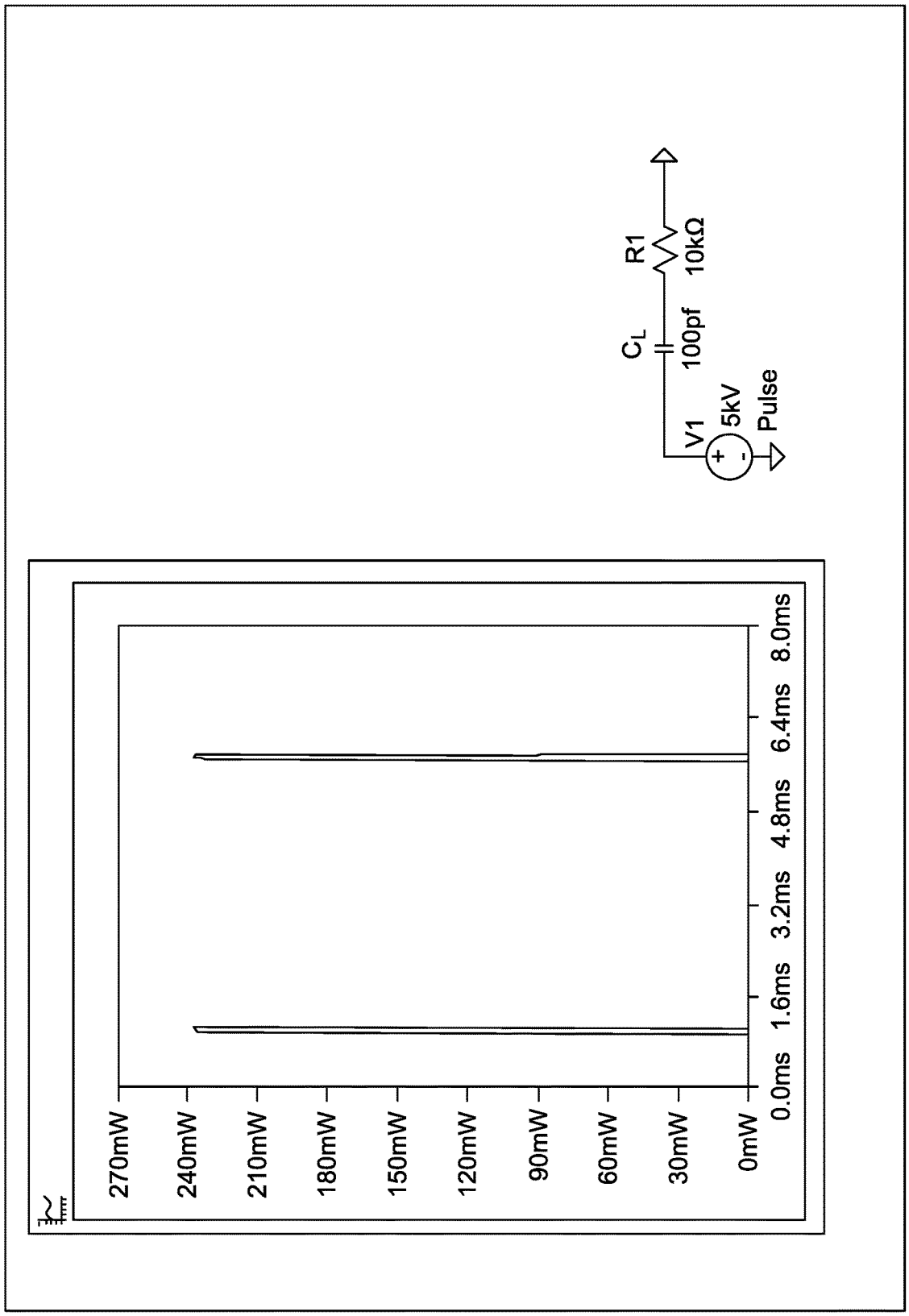
FIG. 3 is a graph depicting the power at the output of the first resistor of the defibrillation protection circuit when a capacitive leadwire of the present disclosure is utilized.

Comparison between the graphs of FIGS. 2 and 3 exemplifies the benefit of using the capacitive leadwires described herein. FIG. 2 depicts the power transferred through the 10 kiloohm resistor $R_1$, which is a typical resistor provided at the input of a defibrillation protection circuit 8, during a 5 kilovolt pulse, which represents a typical defibrillation pulse that might be administered to a patient experiencing cardiac arrest. As can be seen, the resistor $R_1$ encounters about 2.5 kilowatts of power instantaneously at the start of the defibrillation pulse and experiences that power for the duration of the pulse. In the depicted embodiment where the pulse has a duration of approximately 5 milliseconds, the energy transferred through the resistor $R_1$ approaches 13 joules, which is a very large amount of energy in a very short period of time.

This can be compared to the graph in FIG. 3, where the same 5 kilovolt, 5 millisecond pulse is input to a system having a capacitive leadwire 2 connecting between the electrode absorbing the pulse from the patient's chest and the data acquisition device 6. In the depicted embodiment, the capacitor $C_L$ formed by the leadwire 2 has a 100 picofarad capacitance. As demonstrated in the graph, the power measured at the output of the resistor $R_1$ is minimal compared to the configuration without the capacitive leadwire $C_L$, where the power through resistor $R_1$ peaks at about 250 milliwatts at the beginning and end of the defibrillation pulse, and the total energy through the resistor $R_1$ is only about 50 microjoules. Thus, the resistor $R_1$ will not experience heating, and the size of the resistor can even be decreased if desired. The depicted test pulse has a 0.1 millisecond rise and fall time, meaning that the capacitor $C_L$ has time to adjust. However, even if the rise time is much shorter, such as 1 microsecond, the total energy still remains below 2 millijoules, which is still a significant decrease from the 13 joules of energy without the capacitive leadwire 2.

When using the capacitive leadwire 2, the capacitive value of capacitor $C_L$ may be adjusted to ensure that the target frequencies are transmitted and are not filtered out. For example, when utilizing the capacitive leadwire 2 for monitoring respiration, one needs to utilize a high enough carrier frequency that will not be filtered out by the capacitor. For instance, if the carrier frequency is 50 kilohertz (which is common in respiration monitoring), one would use 1 nanofarads capacitor $C_L$. In certain applications, it may be desirable to utilize a higher carrier frequency, such as 1 megahertz, and decrease value of the capacitor $C_L$ to 100 picofarads.

Figure 4A:
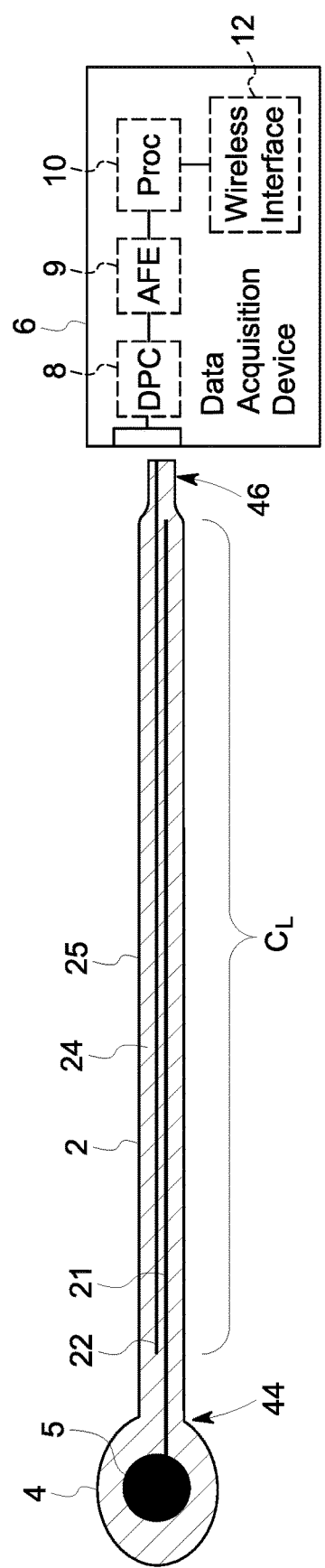
FIGS. 4A-4D depict various embodiments of capacitive leadwires for physiological patient monitoring connecting a chest electrode to a data acquisition device.

FIGS. 4A-4D depict various embodiments of the capacitive leadwire 2. In general, the leadwire 2 has a first conductive layer 21 and a second conductive layer 22 that are galvanically isolated and form a capacitor along the length of the leadwire 2. For example, the first conductive layer 21 and the second conductive layer 22 may be parallel wires divided by a substrate 24, which is an insulator having known dielectric properties. The first conductive layer 21 extends from the electrode end 44 of the leadwire 2, and is in galvanic contact with a conductive portion 5 of the chest electrode 4. The first conductive layer 21 extends along at least a portion of the length of the leadwire 2, and in many embodiments extends for a majority of the length of the leadwire 2. The second conductive layer extends from the device end 46 of the leadwire 2. The second conductive layer 22 also extends at least a portion of the length of the leadwire 2 so that its length sufficiently intersects the length of the first conductive layer 21 so that the two layers can form a capacitor $C_L$. As depicted in FIG. 4A, for example, the cross over area between the first conductive layer 21 and the second conductive layer 22 may form a capacitor $C_L$ that may span a majority of the length of the leadwire 2. In other embodiments, the capacitive area $C_L$ may be larger or smaller compared to the length of the leadwire. In the embodiments depicted and described, the capacitance of the capacitive aspect $C_L$ of the leadwire 2 can be adjusted and controlled by adjusting the area of overlap between the conductive layers 21 and 22 and adjusting the separation between the conductive layers 21 and 22. Furthermore, the capacitance is also affected by the permittivity of the material comprising the substrate 24 between the conductive layers 21 and 22.

In certain embodiments, the leadwire 2 may be formed by printing the conductive layers 21 and 22 on a substrate 24. For example, the conductive layers 21 and 22 may be conductive traces printed on the substrate 24 with conductive ink. Conductive ink is a liquid ink dispensable by a specialized printer to form an object that conducts electricity. The transformation from liquid ink to a solid conductor may involve a drying or curing process. Such inks allow circuits to be drawn or printed on a variety of substrate material, and typically contain conductive materials such as powdered or flaked silver and carbon-like materials, although polymeric conduction is also known. As will be understood by a person having ordinary skill in the art in view of this disclosure, a number of conductive inks are available and appropriate for printing a conductive trace onto a flexible substrate 24 to provide a continuous conductor of a predefined length. The conductive portion 5 of the electrode 4 may also be printed, such as on the substrate material 24.

The flexible substrate 24 may be comprised of any number of materials. In one embodiment, the flexible substrate 24 is a thermal plastic polyurethane (TPU). Alternatively, the flexible substrate 24 may be a polyethylene terephthalate (PET), or any other plastic material sufficiently flexible to be used as a substrate for purposes of providing a leadwire connecting between a chest electrode 4 and a data acquisition device 6.

Figure 4B:
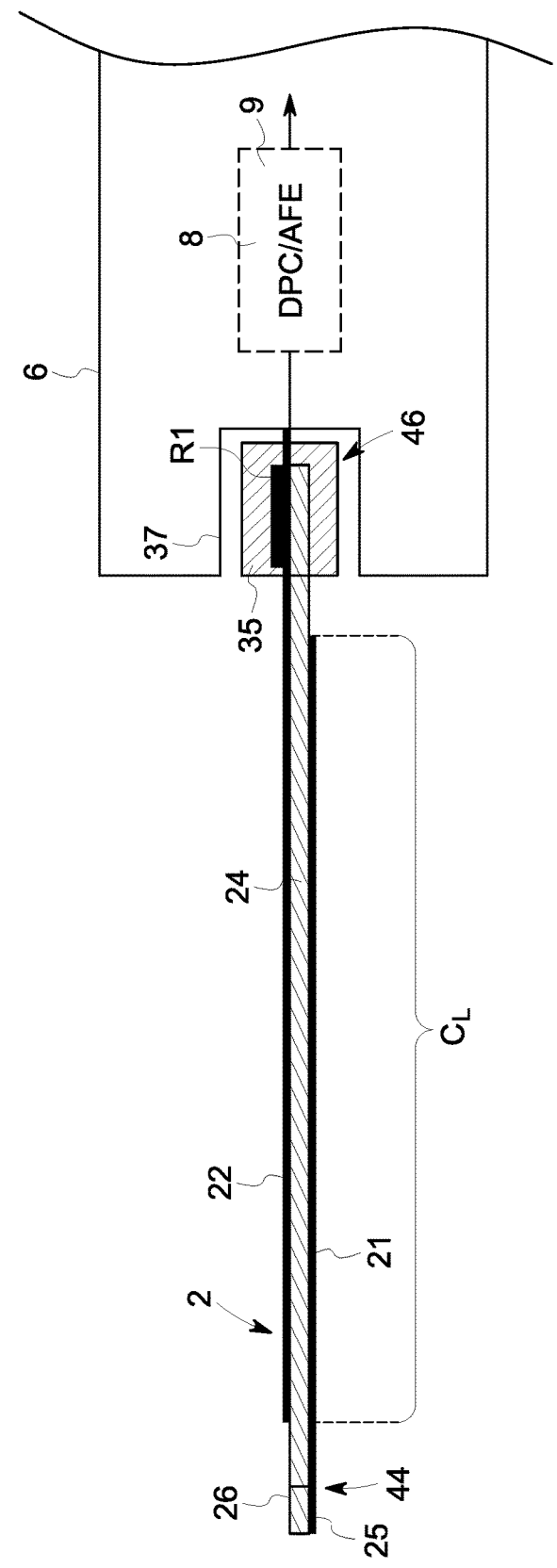
Figure 4C:
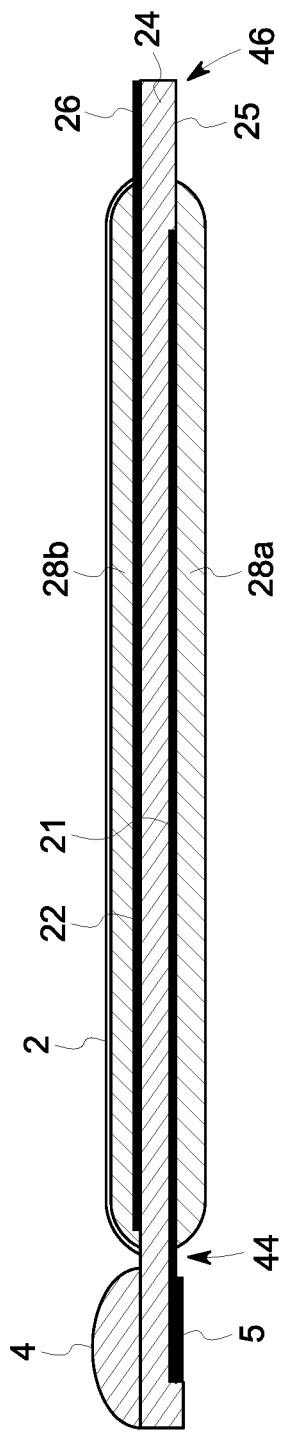

FIGS. 4A and 4B depict different printed embodiments of the leadwire 2. In FIG. 4A, the first conductive layer 21 and the second conductive layer 22 are printed on a first side 25 of a substrate 24. The conductive layers 21 and 22 are parallel printed traces, with the first conductive layer 21 extending from the electrode end 44 and the second conductive layer 22 extending from the device end 46 of the leadwire 2. As described above, the first conductive trace 21 may extend to a conductive portion 5 of an electrode 4, which may also be a printed element.

FIG. 4B depicts a cross sectional view of one embodiment of a capacitive leadwire 2. The first conductive layer 21 is printed on a first side 25 of the strip of substrate, which is for example a long and thin strip of TPU. The first conductive layer is, for example, a first trace printed on the bottom side 25 starting at the electrode end 44 of the leadwire 2 and continuing most of the length of the leadwire 2, as is depicted. A second conductive layer 22 is printed on a second side 26, such as a top side, of the strip of substrate 24. The second conductive layer extends from the device end 46 of the leadwire 2 across most of the length of the leadwire. Accordingly, the first conductive layer 21 and the second conductive layer 22 are separated by the substrate material 24, and thus are galvanically isolated. However, a mutual capacitance between the two adjacent and parallel conductive layers transmits the physiological signals recorded from the patient during normal monitoring operation. However, upon delivery of a defibrillation pulse, the capacitor saturates and the voltage across the capacitor is effectively zero. This is demonstrated in FIG. 3, where the capacitor $C_L$ of the leadwire 2 blocks transmission of the high voltage defibrillation pulse.

The electrode end 44 in the embodiment of FIG. 4B could be provided with an element to connect to an electrode, or an electrode could be formed or attached by any means.

Alternatively, the electrode may be provided with attachment means, such as a clip capable of puncturing any insulation layer and making galvanic connection to the first conductive layer 21.

The geometry of the conductive layer 21, 22 and their arrangement may be varied, whether in a printed embodiment or in a leadwire 2 constructed by other means. For example, the conductive layers 21, 22 may be plate-like, being relatively narrow (such as a width of 1-3 centimeters) and long (such as 1-3 feet) extending the length of the leadwire 2. In other embodiments, the first conductive layer 21 and the second conductive layer 22 may be arranged in a coaxial configuration where one of the conductive layers 21, 22 forms a cylinder surrounding the other conductive layer 21, 22, which is a cylindrical wire, with the substrate material 24 dividing the two layers (e.g., FIG. 4D).

Other elements may also be printed along the length of the leadwire, such as resistive traces or other circuit elements. For example, resistor $R_1$ may be built into the leadwire 2 rather than being incorporated into the defibrillation protection circuit 8 provided in the data acquisition device 6. For example, resistor $R_1$ may be a printed element printed on a top side 26 of the substrate 24 and connected to the second conductive layer 22. In the embodiment of FIG. 4B, the resistor is printed near the device end 46 of the leadwire 2 and is contained within the device connector 35, which is an element configured to be received by and attached to the receptacle 37 of the data acquisition device 6. In other embodiments, the resistor $R_1$ may be printed on a portion of the leadwire 2 that is outside of the device connector 35, and may be anywhere between the capacitor portion $C_L$ of the leadwire 2 and the device end 46. In still other embodiments, the resistor printed on the second conductive layer 22 may be in addition to the resistor $R_1$ of the defibrillation protection circuit 8, and thus may be in series therewith.

Additionally, an insulating layer 28 may be provided over the conductive layers 21 and 22 in order to shield them from noise induced by other magnetic fields, which are common in hospital and other healthcare environments. In the exemplary embodiment of FIG. 4C, which depicts a cross-sectional view of another embodiment of a printed leadwire 2, an insulating layer 28 covers both the conductive layers 21 and 22. Specifically, a first insulating layer 28a is provided on the first side 25 of the substrate 24 and covers the first conductive layer 21. A second insulating layer 28b is provided on the second side 26 of the substrate 24 and covers the second conductive layer 22. Similar to the embodiment described with respect to FIG. 4A, the embodiment in FIG. 4C includes an integrated chest electrode 4, where a conductive portion 5 of the electrode 4 is printed as connected to or as continuously with the first conductive layer 21. The insulating layer 28a covering the first conductive layer 21 stops before the conductive portion 5 of the electrode 4, leaving the conductive portion 5 exposed to allow connection to a patient's skin. Likewise, the top insulating layer 28b may leave the device end 46 of the second conductive layer 22 exposed to allow for connection to the data acquisition device 6.

The insulating layer 28 may be printed over the conductive layers 21, 22 or applied over the conductive layers 21, 22 by other means. For example, the insulating layer 28 may be a separate piece of material adhered to the respective side 25, 26 of the substrate 24. For instance, the insulating layer 28 may be comprised of the same material as the flexible substrate 24, such as TPU or PET, or may be any other material that sufficiently insulates the conductive layers 21, 22 from noise. Alternatively, the insulating layers 28a, 28b may be printed onto the respective side 25, 26 over the respective printed conductive layers 21, 22. For instance, the printed insulating layer 28 may be comprised of ElectrodagPF-455B UV-Curable Insulator Paste by Henkel Corporation or may be 125-17M Screen-Printable UV-Curable Coating by Creative Materials Inc.

Figure 4D:
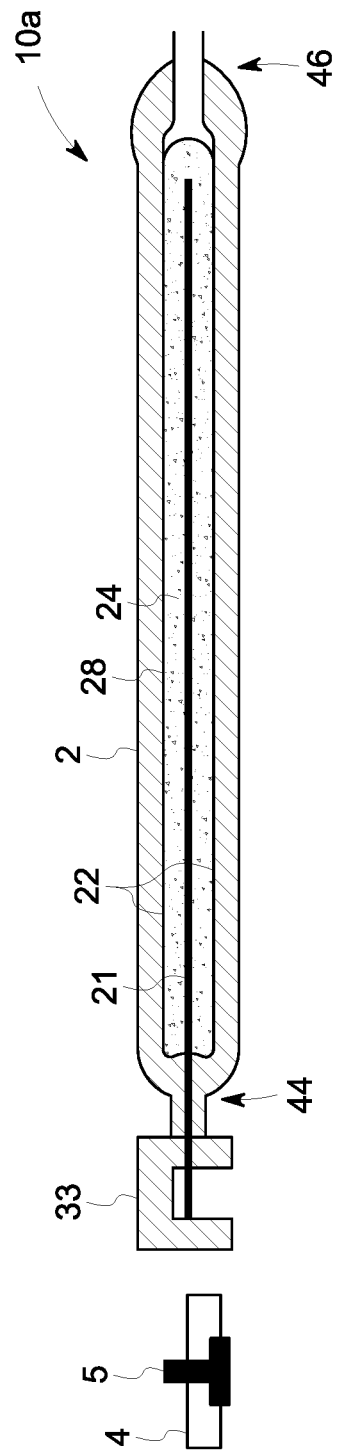

FIG. 4D is a cross-sectional view of another embodiment of a capacitive leadwire 2 where the first conductive layer 21 and the second conductive layer 22 are coaxially arranged. Specifically, the first conductive layer 21 is a wire extending from the electrode end 44 and disposed along the center of the leadwire 2. The second conductive layer 22 is a cylinder surrounding the length of the first conductive layer 21, along the same axis as the wire providing the first conductive layer 21. The substrate material 24 is provided between the first conductive layer 21 and the surrounding second conductive layer 22. The first conductive layer 21 terminates prior to the device end 46 of the leadwire 2, at which point the second conductive layer 22 extends and is exposed to allow connection to the data acquisition device 6. The coaxial arrangement of conductive layers 21 and 22 depicted in FIG. 4D is surrounded by an insulating layer 28. The electrode end 44 is provided with an electrode connector 33, which in the depicted embodiment is a snap connector configured to connect with the conductive portion 5 of a snap electrode 4 which adheres to a patient's skin. In other embodiments, the electrode connector may be any element capable of connecting to an electrode 4, such as an alligator clip or a clamp.

Various monitoring devices and arrangements are known, and a person having ordinary skill in the art will understand that the capacitive leadwires 2 disclosed herein may be applied to any physiological monitoring device where defibrillation protection is desired. In the embodiments, the exemplary data acquisition device 6 serves to collect the physiological data recorded from the patient and transmit the physiological data to a hub device or central patient monitor. Thus, the data acquisition device 6 is equipped with a wireless interface 12 that wirelessly communicates the digitized physiological data to such a hub device or central patient monitor. Specifically, the processor 10 receives the digitized physiological data from the analog front end 9 and controls the wireless interface 12 to transmit the physiological data.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:
1. A leadwire for transmitting physiological potentials, the leadwire comprising:
   an electrode end configured to be connected to an electrode;
   a first conductive layer extending from the electrode end;
   a device end configured to be connected to a data acquisition device;

a second conductive layer extending from the device end; and wherein the first conductive layer is galvanically isolated from the second conductive layer such that the first conductive layer and the second conductive layer form a capacitor that is configured to capacitively transmit physiological potentials from the electrode to the data acquisition device, and wherein an insulating layer of the capacitor extends a majority of a length of the leadwire.

2. The leadwire of claim 1, wherein the first conductive layer and the second conductive layer are parallel wires divided by a substrate.

3. The leadwire of claim 1, wherein the first conductive layer and the second conductive layer are coaxially arranged.

4. The leadwire of claim 1, wherein the first conductive layer and the second conductive layer are comprised of a conductive ink printed on a substrate.

5. The leadwire of claim 4, wherein the first conductive layer is a first trace printed on a first side of the substrate, and the second conductive layer is a second trace printed on a second side of the substrate.

6. The leadwire of claim 5, wherein the substrate is thermoplastic polyurethane.

7. The leadwire of claim 4, wherein the first conductive layer is a first trace printed on a first side of the substrate, and the second conductive layer is a second trace printed on the first side of the substrate.

8. The leadwire of claim 7, wherein the electrode is a printed electrode, and wherein the electrode end of the leadwire is integrally connected to the printed electrode such that the first trace is printed as connected to a conductive portion of the electrode.

9. The leadwire of claim 7, further comprising a resistor printed within the second trace between the capacitor formation with the first trace and the device end.

10. The leadwire of claim 1, wherein the electrode end comprises one of a snap connector, an alligator clip, and a clamp.

11. The leadwire of claim 1, wherein the device end comprises a device connector configured to be received by a corresponding receptacle in the data acquisition device.

12. The leadwire of claim 1, further comprising a resistor within the second conductive layer between the capacitor formation with the first conductive layer and the device end.

13. A printed leadwire comprising:
a first conductive layer printed on a substrate, the first conductive layer extending from an electrode end configured to be connected to an electrode; and
a second conductive layer printed on the substrate, the second conductive layer extending from a device end configured to be connected to a data acquisition device;
wherein the first conductive layer is galvanically isolated from the second conductive layer such that the first conductive layer and the second conductive layer form a capacitor that capacitively transmits physiological potentials having a frequency below 1 MHz from the electrode end to the device end, and
wherein an insulating layer of the capacitor extends a majority of a length of the leadwire.

14. The printed leadwire of claim 13, wherein the first conductive layer is a first trace printed with conductive ink on a first side of the substrate, and the second conductive layer is a second trace printed with conductive ink on a second side of the substrate.

15. The printed leadwire of claim 13, wherein the first conductive layer is a first trace printed with conductive ink on a first side of the substrate, and the second conductive layer is a second trace printed with conductive ink on the first side of the substrate.

16. The printed leadwire of claim 13, further comprising a conductive portion of an electrode printed on the substrate and connected to the first conductive layer.

17. The printed leadwire of claim 13, further comprising a resistor connected to the second conductive layer between the capacitor formation with the first conductive layer and the device end.

18. A leadwire for transmitting physiological potentials, the leadwire comprising:
an electrode end configured to be connected to an electrode;
a first conductive layer extending from the electrode end;
a device end configured to be connected to a data acquisition device;
a second conductive layer extending from the device end; and
wherein the first conductive layer is galvanically isolated from the second conductive layer such that the first conductive layer and the second conductive layer form a capacitor that is configured to capacitively transmit physiological potentials having a frequency below 1 MHz from the electrode to the data acquisition device, and
wherein the electrode end comprises one of a snap connector, an alligator clip, and a clamp.

* * * * *